(12) United States Patent
Ostermeier et al.

(10) Patent No.: US 8,948,475 B2
(45) Date of Patent: Feb. 3, 2015

(54) METHOD FOR COMPUTING A COLOR-CODED ANALYSIS IMAGE (75) Inventors: Martin Ostermeier, Buckenhof (DE); Marcus Pfister, Bubenreuth (DE); Thomas Redel, Poxdorf (DE)

(73) Assignee: Siemens Aktiengesellschaft, Munich (DE)

( * ) Notice: Subject to any disclaimer, the term of this patent is extended or adjusted under 35 U.S.C. 154(b) by 735 days.

(21) Appl. No.: 12/825,785

(22) Filed: Jun. 29, 2010

(65) Prior Publication Data

US 2010/0329523 A1 Dec. 30, 2010

(30) Foreign Application Priority Data

Jun. 30, 2009 (DE) .......................... 10 2009 031 141

(51) Int. Cl.
G06K 9/00 (2006.01)
A61B 6/00 (2006.01)
G06T 11/00 (2006.01)

(52) U.S. Cl.
CPC ................. *A61B 6/504* (2013.01); *A61B 6/463* (2013.01); *A61B 6/5235* (2013.01); *G06T 11/001* (2013.01); *A61B 6/503* (2013.01)
USPC ........................................................ 382/128

(58) Field of Classification Search
USPC .................................................. 382/128–132
See application file for complete search history.

(56) References Cited

U.S. PATENT DOCUMENTS 6,909,792 B1 * 6/2005 Carrott et al. ................. 382/128
8,620,049 B2 * 12/2013 Leiblein et al. .............. 382/130
2007/0041625 A1 * 2/2007 Camus et al. ................ 382/130
2008/0033285 A1 * 2/2008 Camus et al. ................ 600/425

(Continued)

FOREIGN PATENT DOCUMENTS

DE 10000185 A1 7/2001
DE 102005036564 A1 2/2007

(Continued)

OTHER PUBLICATIONS

Urban Malsch, Hartmut Dickhaus, Helmut Kücherer; Quantitative Analyse von koronarangiographischen Bildfolgen zur Bestimmung der Myokardperfusion; Bildverarbeitung für die Medizin 2003—Algorithmen—Systeme—Anwendungen; Springer-Verlag, pp. 81-85.

(Continued)

*Primary Examiner* — Mark Holcomb
*Assistant Examiner* — Jonathan K Ng (57) ABSTRACT A method for computing a color-coded analysis image of an examination area of an examination object from a temporal sequence of fluoroscopic images of the examination area comprising a vascular system containing arteries and/or veins is provided. An acquisition time instant has been assigned to each of the fluoroscopic images representing a given distribution of a material embolizing some of the vascular system. The fluoroscopic image spatially corresponds to an analysis image pixel by pixel. A computer receives the fluoroscopic images with a color attribute assigned to each pixel of the analysis image at an image point and a time instant. If a pixel differs from a pixel at a preceding time instant, the color attribute assumes a color attribute of the time instant and the difference. If a pixel corresponds to a background color of the analysis image, the color attribute assumes a background color.

9 Claims, 6 Drawing Sheets

(56) References Cited

U.S. PATENT DOCUMENTS

| | | | | |
|---|---|---|---|---|
| 2008/0051648 A1* | 2/2008 | Suri et al. | | 600/407 |
| 2010/0329526 A1* | 12/2010 | Pfister et al. | | 382/130 |
| 2011/0311113 A1* | 12/2011 | Baumgart | | 382/128 |

FOREIGN PATENT DOCUMENTS

| | | | |
|---|---|---|---|
| DE | 102006025420 A1 | 12/2007 | |
| DE | 102007024450 A1 | 11/2008 | |
| EP | 1345154 A1 | 9/2003 | |

OTHER PUBLICATIONS

Endovaskuläre Behandlung zerebraler AV-Malformationen; AWMF online /Arbeitsgemeinschaft der Wissenschaftlichen Medizinischen Fachgesellschaften http://www.uni-duesseldorf.de/awmf/ll/047-014.htm; 2004.

2008J18065; Farbkodierte Darstellung zeitlich veränderlicher Bildinhalte in der Röntgen-Durchleuchtung/Roadmap während minimalinvasiver Interventionen.

2009J06853; Kontinuierlich aktualisierte Roadmaps (z.B. für Embolisation).

* cited by examiner

METHOD FOR COMPUTING A COLOR-CODED ANALYSIS IMAGE

CROSS REFERENCE TO RELATED APPLICATIONS

This application claims priority of German application No. 10 2009 031 141.6 filed Jun. 30, 2009, which is incorporated by reference herein in its entirety.

FIELD OF THE INVENTION

The present invention relates to a method for computing a color-coded analysis image of an examination area of an examination object from a temporal sequence of x-ray images of the examination area. The examination area comprises a vascular system comprising arteries and/or veins as blood vessels. The x-ray images and the analysis image corresponding spatially with each other pixel by pixel. the invention also relates to corresponding device.

BACKGROUND OF THE INVENTION

Figure 1:
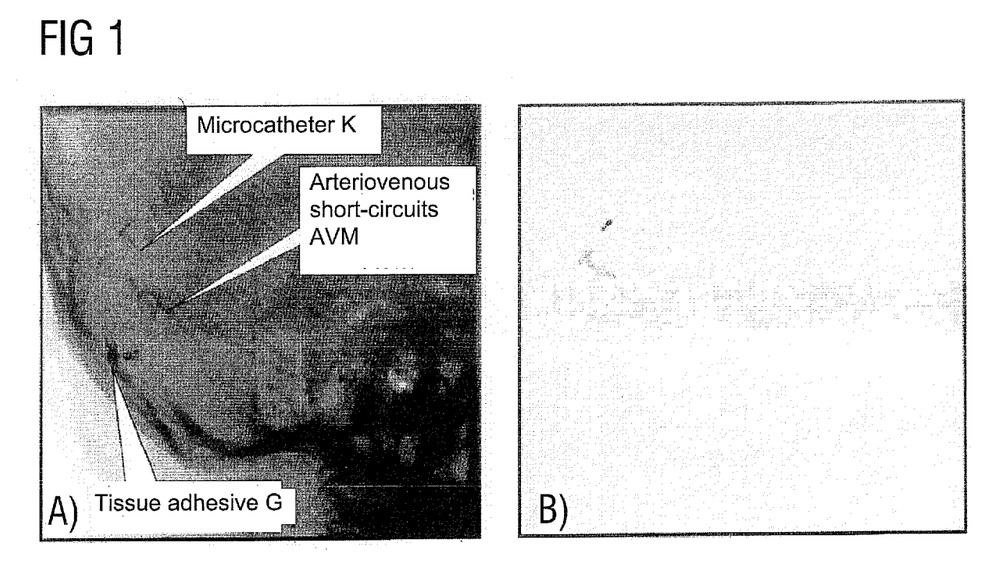
FIG. 1 shows a native fluoroscopic image A) and a frame B) subtracted from this.

During an intervention on an angiography system, for instance in order to navigate the instruments (e.g. in the head or heart), real-time images are obtained using fluoroscopy. An intervention that is frequently performed on such a system is the embolization of tumors or arteriovenous malformations (AVM) as shown in FIG. 1.

Arteriovenous malformations (AVM) are congenital malformations of the vascular system, often malformations of the vascular system of the central nervous system, the brain or the facial skeleton. In such a malformation there is a direct connection between the arteries and the veins of the vascular system. Hence between the arteries and the veins there are no capillary vessels in which the actual material transfer takes place between the blood and tissue. One consequence of this is that the tissue area concerned is not supplied with blood. Another consequence is that the pressure rises in the veins, which can cause them to enlarge and potentially result in hemorrhaging. In particular, brain hemorrhages may be highly critical here.

There are three techniques available today for treating AVM, which are mostly also used in combination. These treatments are neurosurgical operations, radiation treatment and endovascular therapies. Whatever the type of AVM treatment, it is necessary to have precise knowledge of the position, shape and form of the AVM and of the detailed blood-flow conditions in order to plan and carry out the treatment. Hence both morphological information (position, shape and type of blood vessels) and functional time-dependent information (flow conditions) is required.

Computer tomography and magnetic resonance tomography in particular are possible as non-invasive imaging modalities for diagnosis. Often an angiography is also carried out in order to obtain precise information and plan treatment in detail. In this case there are two alternatives available: C-arm based imaging that is static in time and spatially resolved in three dimensions or imaging that is time-resolved in one dimension and spatially resolved in two dimensions.

Interventional endovascular therapy is performed in the angiography laboratory using fluoroscopy. Angiography views (in particular DSA views) through the relevant vascular region are produced for planning and checking. The views can be recorded on monoplane equipment, although biplane equipment, which records two views in parallel from different angulations, are more suitable. Analysis can be performed on each of the two views It is important here to track the continuous progress of the embolization, particularly in order to prevent the embolic agent flowing back into unaffected vessels. Usually such procedures are monitored using subtracted frames, in which only the differences from a specific mask image are visible, as shown in illustration B) of FIG. 1) by way of example. One advantage of this is that anatomic backgrounds are "canceled out". In addition, the progress of the embolization can be monitored more easily, because after the mask is re-initialized, the mask and also the embolic agent that has accumulated up until this instant is no longer visible in the (subtracted) frame sequences.

This can be a disadvantage, however, because after the mask is re-initialized, the doctor can no longer identify the areas that have already been embolized. It is also advantageous for the doctor not to see the newly embolized areas as a "growing black region". What is important to the doctor is to be able to assess the progress, i.e. identify at a glance which area has been embolized before the others or where newly injected embolic agent has accumulated.

Usually a "roadmap" technique can be used. In other words, a native mask is recorded, which is subtracted from the subsequent live X-ray images, i.e. during the intervention, in order to show changes. If a continuous process is to be viewed, this mask may need to be constantly re-initialized manually.

DE 10 2007 024 450 A1 discloses a method for computing a color-coded first analysis image. A computer receives a temporal sequence of X-ray images, each of which is assigned an acquisition time instant and each of which represents a given contrast-agent distribution in the examination area of an examination object at the respective acquisition time instant. The examination object comprises a vascular system and tissue supplied with blood via the vascular system. The computer computes a characteristic value for each pixel of an analysis image, which corresponds uniquely to one of the blood vessels of the vascular system (single-vessel pixel), for each of the x-ray images, from the data values of the pixels of the respective x-ray image that lie in a first analysis core that is defined by the respective single-vessel pixel and has the same spatial position in all the X-ray images. The x-ray images and the first analysis image correspond spatially with each other pixel by pixel. For each single-vessel pixel, the computer uses the variation over time of the characteristic values of the respective single-vessel pixel to calculate a characteristic time instant for the arrival time of the contrast agent at the respective single-vessel pixel. In addition, it assigns each single-vessel pixel a color attribute that is characteristic of the respective characteristic time instant and assigns every other pixel a color attribute that does not depend on the characteristic time instant. The computer outputs to a user the analysis image color-coded in this manner. A specific color coding is proposed here for each mask re-initialization, but any continuity in the color coding is not reflected.

SUMMARY OF THE INVENTION

The object of the present invention is to create possible means for making it easier to identify time-continuous information on the embolization in the blood vessels.

This object is achieved by the features given in the independent claims. The dependent claims disclose advantageous developments.

The present invention achieves this object using, amongst other means, color coding, which represents as a color progression (i.e. coding) the progress of an embolization between two re-initializations of the roadmap masks and also prior to the re-initializations of the masks. This can be done on a pixel-by-pixel basis, or else pixels can also be combined into larger areas. In this solution, pixels that correspond to at least one of the blood vessels of the vascular system and/or represent tissue adhesive have a different color coding from background pixels that do not correspond either with the blood vessels of the vascular system or with the tissue adhesive.

Hence, in other words, it is provided according to the invention to view an attribute of the value of the pixels, namely the color attribute. For example, it can be provided here that a check of whether the pixel has a value indicating accumulation of the embolizing material is used as a color attribute. If there is a difference from the previous image, this means that the time instant t of the image currently being viewed is the time instant at which the embolizing material arrived for the first time at the point defined by the pixel. This time instant can then be saved as a color index $F(i,j)$: $F(i,j)=t$. The color index assigned to a pixel, which ultimately defines the color of the analysis image, hence indicates whether a pixel corresponds to the background (i.e. not the embolizing material) or, if it is a pixel indicating the presence of the embolizing material, at what time the pixel first indicated embolizing material, i.e. typically was "dark". As the person skilled in the art knows, the query relating to a color property such as "presence of the embolizing material"="dark pixel" can be implemented as a threshold query, for example.

The color index now defines in the visualization of the color-coded analysis image the color in which the corresponding pixel is displayed, which means that the color index is mapped onto a color by a function $K(T)$ at the time instant T to which the analysis image relates. In particular, it can be provided that the coloration of a pixel having a color index that differs from the value corresponding to the background, i.e. from the characteristic value for a background color, is selected as a function of the difference between the time instant t defined by the color index and the time instant T of the analysis image. This means, however, that if, for example, the analysis image is generated at different time instants T, it can be seen by looking at these images how far in the past the embolizing material was found to be there for the first time. The color then changes from time instant T to time instant T.

It can also be provided that a pixel having a color index that differs from the characteristic value for a background color is colored in a specified color if the time instant t defined by the color index lies prior to a last-performed refresh of a mask image. Hence if a roadmap is re-initialized, all pixels already indicating embolizing substance prior to this time instant can be represented in a different color, for instance purple.

In an exemplary embodiment, it can hence be provided that for each fluoroscopic image, recorded at a time instant t prior to a time instant T, of the sequence, in a temporal sequence a check is performed for each pixel (i,j,t), by comparing with the previous fluoroscopic image in time, as to whether the pixel assumes at time instant t a value indicating the accumulation of the embolizing material (comparison of color attribute), in which case for such a value, the time instant t is saved as a color index for this pixel, and a check is performed for each pixel (i,j,t) as to whether the pixel has a value that corresponds to the background, in which case the color index is set to a value indicating a background, wherein, for the purpose of computing the color-coded analysis image at time instant T, each pixel of the analysis image is colored as a function of the color index using a color curve $K(T)$.

The analysis image can also always be kept updated by recording a new fluoroscopic image of the sequence, so as to provide a user with means to track development during the intervention. The comparison then need only be performed for the most recent and the previous image in order to obtain the current color indices.

According to the invention, the method can be performed by a computer. The computer can output at least one color-coded analysis image to the user as a result of the executed method.

BRIEF DESCRIPTION OF THE DRAWINGS

Further advantages, details and developments of the invention are given in the following description of exemplary embodiments in conjunction with the drawings, in which using schematic diagrams by way of example.

DETAILED DESCRIPTION OF THE INVENTION

Arteriovenous malformations AVM are identified in FIG. 1 A). A microcatheter K inserted selectively into the supplying artery introduces tissue adhesive G (e.g. onyx) in order to close the arteriovenous short-circuits or malformations. A) shows the native fluoroscopic image, FIG. 1 B) shows the correspondingly subtracted frame (roadmap), on which are visible only the differences from a specific mask image. Roadmap images are mainly composed of "neutral" background (namely the parts in which the live image (image frame during the intervention) is identical to the mask and which hence "cancel themselves out"), and the changes in the live image compared with the mask, which stand out as dark areas (see illustration B). Artifacts may also show up as white points.

Figure 2:
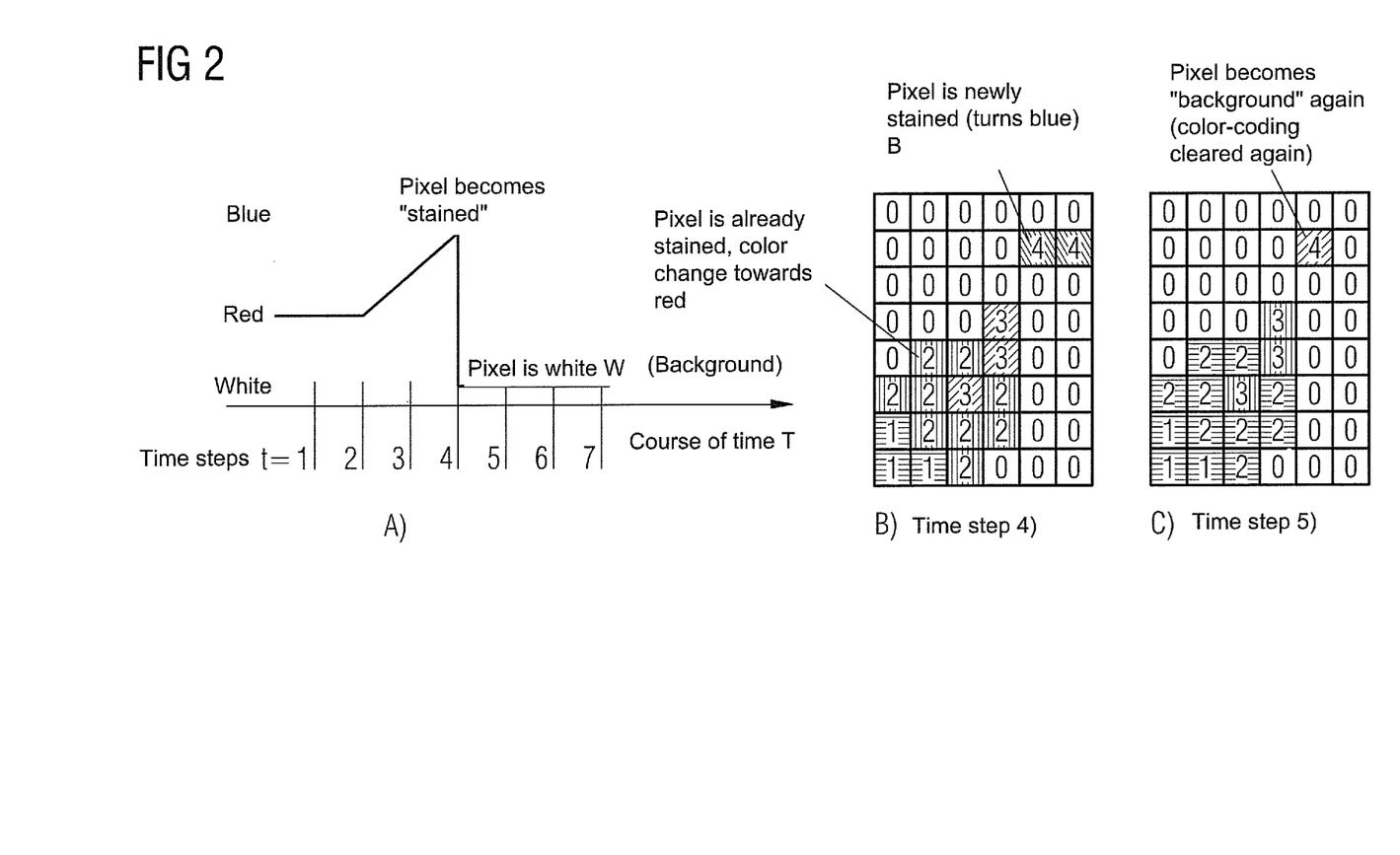
FIG. 2 shows in illustration A) by way of example a time/color curve for image pixels, in illustration B) a schematic view of an image segment in time step 4 of the indicated time sequence from time step 1 to 7, and in illustration C) the same image segment in a time step 5 later than time step 4.

According to the invention, it is noted for each image pixel the time instant at which the image pixel becomes "dark" for the first time, which in the intervention corresponds to an accumulation of embolizing material or embolic agent (e.g. tissue adhesive) at this location. FIG. 2 shows this clearly.

A) shows by way of example a "time/color curve" for each pixel (over seven time steps or time instants). B) shows schematically an image segment in time step t=4. Each of the pixels shown contains the piece of information on when it became dark initially (where "0" is used to code the background pixels in the example.) Some of the pixels have become dark in the current time step 4 (hence tissue adhesive has accumulated here). They bear the number "4" as the piece of information. Some of the pixels have been dark for a longer time; they consequently bear the numbers "1" to "3" as the piece of information. The pixels are assigned a color in accordance with the color curve. C) shows the same segment one time step later. One of the pixels that was stained in step "4" is "light" again in the current image; the piece of information is then reset to "background" (i.e. "0"). Otherwise the information remains the same, with the color coding moving in the "red" R direction in accordance with the color curve.

Expressed formally, let "pixel(i,j,t)" be an image pixel at the image point (i,j) at time instant t, and F(i,j) be the corresponding "color index". Then the color coding comprises simply the following queries

```
IF    pixel(i,j,t) "is darker than" pixel (i,j,t-1)
THEN  F(i,j) := t;
IF    pixel(i,j,t) "corresponds to background"
THEN  F(i,j) := H;
``` where "H" stands for a background-coding value, e.g. H=0.

For visualization at time instant T, each pixel(i,j,T) is now simply coded according to its color index F(i,j) and the corresponding color curve K(T) (FIG. 2). The principle that applies here is that the coloring of a pixel reflects how many time intervals ago T-t it became stained.

In the present embodiment, pixels that are just becoming "dark" are coded "blue" B. The longer they remain dark, the "redder" they become. If a pixel becomes light again, the color coding is also reset to "background" i.e. white or number "0".

Figure 3:
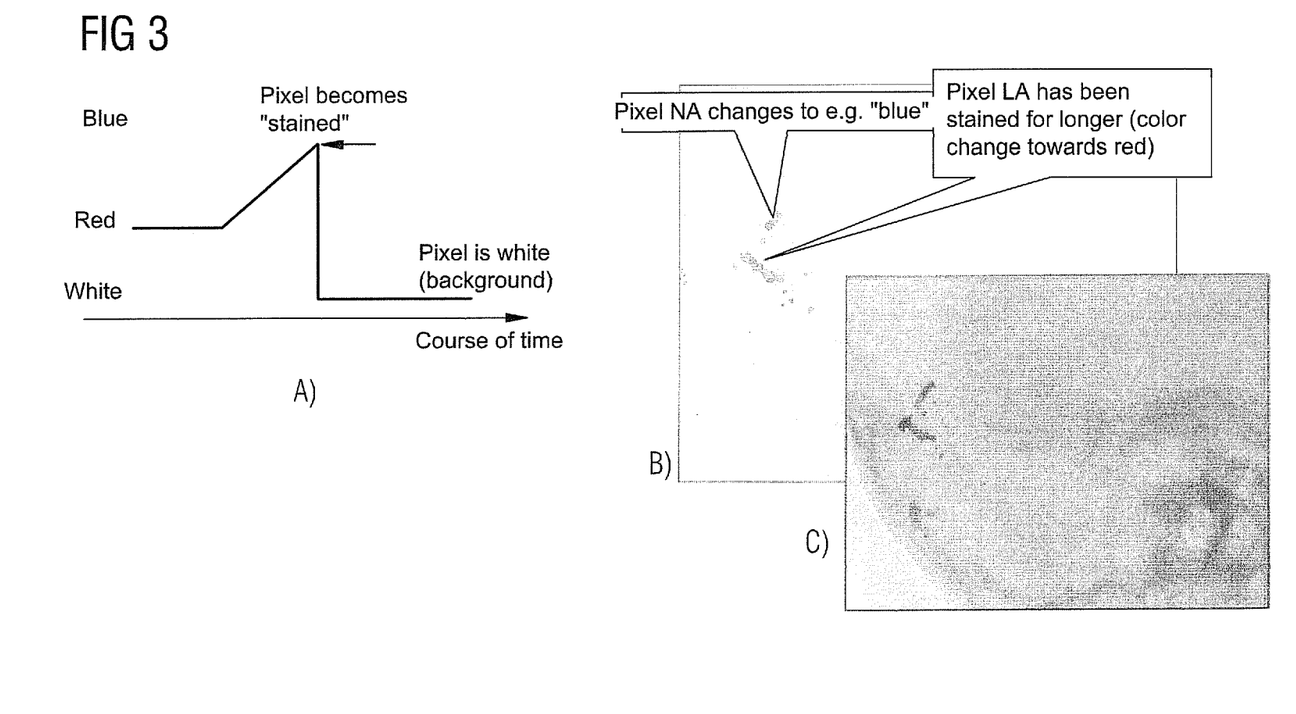
FIG. 3 shows in illustration A) by way of example a time/color curve for image pixels, in illustration B) an image from an embolization sequence, and in illustration C) a color-coding superimposed on a live image.

FIG. 3 shows in A) by way of example a corresponding time/color curve for each pixel and in B) an example from an embolization view.

If tissue adhesive accumulates in a location, the image area (i.e. the corresponding pixels) becomes dark, this time instant is saved for each pixel, the color coding of these pixels NA is initially set to "blue". The color coding now continues to show how long the tissue adhesive has already been accumulating. The longer the region remains stained, the more the color changes from "blue" towards "red". If a pixel becomes "light" again, e.g. because the adhesive was only briefly and temporarily in the area, the color coding is reset to background.

In further embodiments, the color coding can be superimposed on the live fluoroscopic image, as is shown in C) in FIG. 3 for instance. The superposition can be faded in or out using a slide control.

Figure 4:
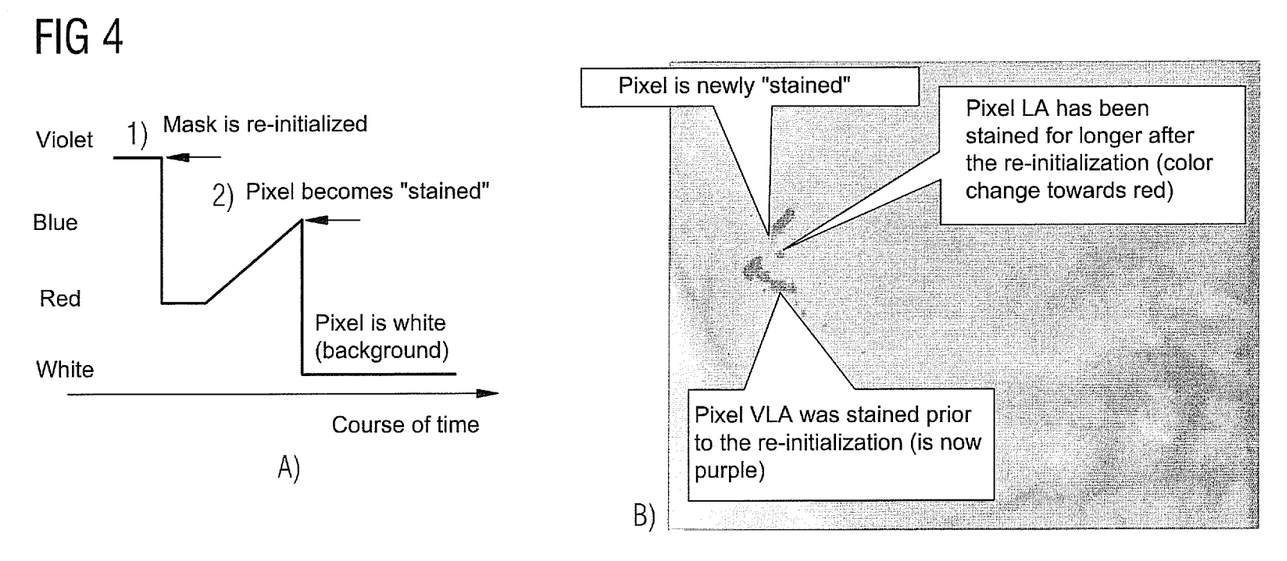
FIG. 4 shows in illustration A) by way of example a time/color curve for image pixels in the event of a mask re-initialization, in illustration B) an image from an embolization sequence, and in illustration C) a color-coding superimposed by a live image.

In further embodiments, the color coding can also be combined with a re-initialization of the roadmap masks. FIG. 4 A) shows an example of a corresponding "time/color curve". B) shows a corresponding image from an embolization sequence, where the color coding is superimposed on the live image.

If the mask is re-initialized, all of the pixels VLA stained up until this time change color, in this example to "purple". For all other pixels LA, color coding now continues as proposed above, i.e. the change after a re-initialization is documented. If an intensity changes in the mask area (for instance if areas that are already embolized become "more" concentrated with tissue adhesive), this can additionally be shown by a color change in the mask pixels.

In addition, the gray level of a pixel of the subtracted image can be coded as the brightness level for the color-coded pixel.

Figure 5:
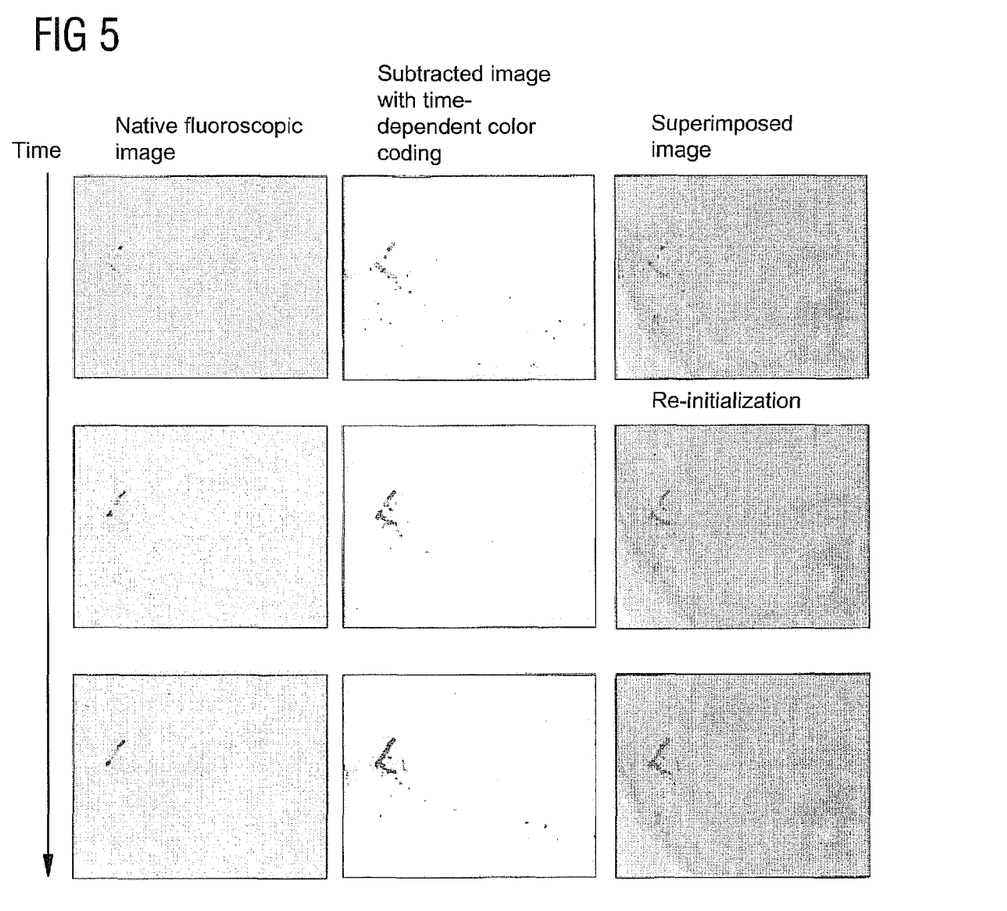
FIG. 5 shows an image sequence over the course of time, in which the color coding and its variation is shown in gray levels and in color.

FIG. 5 shows an image sequence (native fluoroscopy image, subtracted image, superimposed live image) over the course of time, which illustrates the color coding and its change in accordance with the above explanations.

According to the invention, the method can be performed by a computer.

Figure 6:
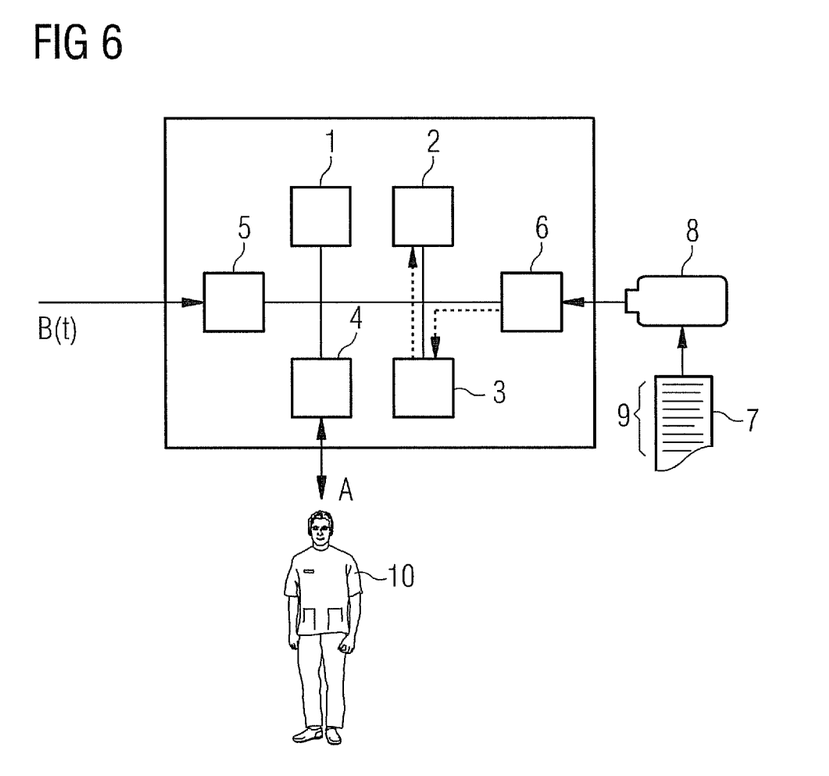
FIG. 6 shows a block diagram of an analysis arrangement.

As shown in FIG. 6, such a computer is composed of standard components 1 to 6. In particular, the computer has a microprocessor 1, a random access memory (RAM) 2, a mass storage device 3 (for example a hard disk), a user interface 4, a data interface 5 and a programming interface 6. The components 1 to 6 have a standard design and work together in a standard manner. Hence, for instance, the user interface 4 can comprise standard input and output devices such as a keyboard, a mouse, a display device etc. The data interface 5 may be an Internet interface or a LAN interface or a USB interface, for example. Also an embodiment as a drive for an interchangeable medium (for instance a CD-ROM or a DVD) is possible. Similar embodiments are possible for the programming interface 6. If applicable, the data interface 5 and the programming interface 6 can be combined into a shared interface.

A computer program 7 is input to the computer via the programming interface 6. For instance, a data storage medium 8, on which the computer program 7 is stored in machine-readable form, can be connected to the computer. The computer program 7 is then read from the data storage medium 8 and copied into the mass storage device 3 of the computer, where it is also stored.

The computer program 7 contains machine code 9, i.e. program instructions that can be executed by the computer directly and immediately. A user can start the computer program 7 using standard input commands (for instance a double mouse-click). When the computer program 7 is started, it is loaded into the RAM 2 of the computer and executed by the computer. The execution of the computer program 7 by the computer results in the computer performing a computation method, which is described in detail above in connection with the other figures.

The computer can receive a sequence of fluoroscopic or X-ray images B and their acquisition time instants t, and compute an analysis image A from the sequence. The computer can output the color-coded analysis image A to the user 10.

In a further embodiment, the computer can output to the user simultaneously with the color-coded analysis image another color-coded analysis image.

The computer can receive a further temporal sequence of fluoroscopic images and compute the color-coded further analysis image from the further temporal sequence in a similar manner to that for the first said color-coded analysis image.

The difference from the procedure described above is that, although the further sequence of X-ray images are X-ray images of the same examination object and of the same examination area of the examination object, and have also been taken with the same frame geometry, the acquisition of the further sequence took place at a different time instant from the acquisition of the first said sequence.

The computer can display the two analysis images side-by-side or superimposed on each other for example. It is also possible for the computer to compute the differences between the two analysis images and output the difference image to the user 10.

The present invention has numerous advantages. In particular, it is possible to display primarily visually in a single analysis image the vascular architecture of arteries and veins and moreover the functional information on the embolization. Hence the user no longer needs to combine the data mentally. In addition, the changing flow conditions of the embolic agent can also be identified clearly during and after an intervention and can be incorporated in subsequent intervention planning.

In general, the method described above can also be used for other vascular malformations (e.g. fistulas, aneurysms, stenoses etc.), and even neoplastic changes in the brain and even other regions of the body.

The above description is used solely to explain the present invention. The scope of protection of the present invention, however, shall be defined solely by the attached claims.

The invention claimed is:

1. A method for computing an analysis image of an examination area of an examination object from a temporal sequence of fluoroscopic images of the examination area, wherein the examination area comprises a vascular system including arteries and/or veins as blood vessels, and wherein the analysis image spatially corresponds to the fluoroscopic images pixel-by-pixel, comprising:
    assigning an acquisition time instant to each of the fluoroscopic images representing a given distribution of a material embolizing at least some of the vascular system in the examination area at the acquisition time instant;
    receiving the temporal sequence of fluoroscopic images by a computer;
    assigning a color attribute to a pixel of the analysis image at the acquisition time instant by the computer with a rule of:
        assigning a color to the pixel at the analysis image if the pixel at the acquisition time instant first time becomes darker than the pixel at a preceding acquisition time instant indicating the pixel is stained,
        changing the color of the pixel at the analysis image if the pixel at the acquisition time instant remains dark from the preceding acquisition time instant based on how many time intervals ago the pixel first time becomes darker, and
        assigning a background color to the pixel at the analysis image if the pixel at the acquisition time instant corresponds to a background color of the analysis image;
    computing the analysis image repeatedly after re-initializing the temporal sequence of the fluoroscopic images by the computer with a further rule of:
        changing color of pixels that are stained until the re-initialization to a different color, and
        assigning a color attribute to other pixels with the rule prior to the re-initialization; and
    outputting the analysis image to a user.

2. The method as claimed in claim 1, wherein the analysis image is visually displayed to the user on a display device of the computer.

3. The method as claimed in claim 1, wherein the color attribute changes gradually with time.

4. The method as claimed in claim 1, wherein a gray level image of the vascular system is superimposed on the analysis image by the computer.

5. The method as claimed in claim 1, wherein a gray level of a pixel is additionally incorporated in a color coding of the analysis image as a brightness value.

6. The method as claimed in claim 1, wherein an analysis area is selected by the user and the analysis image is only computed within the analysis area by the computer.

7. A non-transitory computer program stored on a data medium and executable by a computer for computing an analysis image of an examination area of an examination object from a temporal sequence of fluoroscopic images of the examination area, wherein the examination area comprises a vascular system including arteries and/or veins as blood vessels, and wherein the analysis image spatially corresponds to the fluoroscopic images pixel-by-pixel, comprising:
    a machine code for:
        assigning an acquisition time instant to each of the fluoroscopic images representing a given distribution of a material embolizing at least some of the vascular system in the examination area at the acquisition time instant;
        receiving the temporal sequence of fluoroscopic images;
        assigning a color attribute to a pixel of the analysis image at the acquisition time instant with a rule of:
            assigning a color to the pixel at the analysis image if the pixel at the acquisition time instant first time becomes darker than the pixel at a preceding acquisition time instant indicating the pixel is stained,
            changing the color of the pixel at the analysis image if the pixel at the acquisition time instant remains dark from the preceding acquisition time instant based on how many time intervals ago the pixel first time becomes darker, and
            assigning a background color to the pixel at the analysis image if the pixel at the acquisition time instant corresponds to a background color of the analysis image;
        computing the analysis image repeatedly after re-initializing the temporal sequence of the fluoroscopic images by the computer with a further rule of:
            changing color of pixels that are stained until the re-initialization to a different color,
            assigning a color attribute to other pixels with the rule prior to the re-initialization; and
        outputting the analysis image to a user.

8. A computer for computing an analysis image of an examination area of an examination object from a temporal sequence of fluoroscopic images of the examination area, wherein the examination area comprises a vascular system including arteries and/or veins as blood vessels, and wherein the analysis image spatially corresponds to the fluoroscopic images pixel-by-pixel, comprising:
    a storage device that stores a computer program for:
        assigning an acquisition time instant to each of the fluoroscopic images representing a given distribution of a material embolizing at least some of the vascular system in the examination area at the acquisition time instant;
        receiving the temporal sequence of fluoroscopic images;
        assigning a color attribute to a pixel of the analysis image at the acquisition time instant with a rule of:
            assigning a color to the pixel at the analysis image if the pixel at the acquisition time instant first time becomes darker than the pixel at a preceding acquisition time instant indicating the pixel is stained,
            changing the color of the pixel at the analysis image if the pixel at the acquisition time instant remains dark from the preceding acquisition time instant based on how many time intervals ago the pixel first time becomes darker, and assigning a background color to the pixel at the analysis image if the pixel at the acquisition time instant corresponds to a background color of the analysis image;

computing the analysis image repeatedly after re-initializing the temporal sequence of the fluoroscopic images by the computer with a further rule of:

changing color of pixels that are stained until the re-initialization to a different color, assigning a color attribute to other pixels with the rule prior to the re-initialization; and outputting the analysis image to a user.

9. The method as claimed in claim 1, wherein a blue color is assigned to the pixel if the pixel at the acquisition time instant first time becomes darker than the pixel at the preceding acquisition time instant, wherein the color of the pixel changes more from blue to red if the pixel remains dark longer in the time intervals, and wherein the pixel is reset to the background color if the pixel becomes light again.

* * * * *